United States Patent [19]

Anderson et al.

[11] Patent Number: 5,698,724
[45] Date of Patent: Dec. 16, 1997

[54] AMINO ACID METAL COMPLEXES USING HYDROLYZED PROTEIN AS THE AMINO ACID SOURCE AND METHODS RE SAME

[75] Inventors: Michael D. Anderson; Mahmoud M. Abdel-Monem, both of Eden Prairie, Minn.

[73] Assignee: Zinpro Corporation, Eden Prairie, Minn.

[21] Appl. No.: 640,332

[22] Filed: Apr. 30, 1996

[51] Int. Cl.$^6$ .............. C07F 3/06; C07F 1/08; C07F 15/00

[52] U.S. Cl. .............. 556/50; 556/63; 556/116; 556/134; 556/148

[58] Field of Search .............. 556/134, 116, 556/148, 50, 63

[56] References Cited

U.S. PATENT DOCUMENTS

| | | | |
|---|---|---|---|
| 2,555,276 | 5/1951 | Pattee | 260/529 |
| 2,657,232 | 10/1953 | Borkenhagen | 260/529 |
| 2,960,406 | 11/1960 | Cardon | 99/2 |
| 3,168,541 | 2/1965 | Hobbs | 260/439 |
| 3,396,104 | 8/1968 | Miller | 210/54 |
| 3,463,858 | 8/1969 | Anderson | 424/289 |
| 3,775,132 | 11/1973 | Richards, Jr. | 426/364 |
| 3,925,433 | 12/1975 | Abdel-Monem et al. | 260/438.5 R |
| 3,941,818 | 3/1976 | Abdel-Monem | 260/429.9 |
| 3,950,372 | 4/1976 | Abdel-Monem | 260/429 R |
| 3,969,540 | 7/1976 | Jensen | 426/657 |
| 4,020,158 | 4/1977 | Ashmead et al. | 424/177 |
| 4,021,569 | 5/1977 | Abdel-Monem | 424/289 |
| 4,067,994 | 1/1978 | Anderson et al. | 424/295 |
| 4,103,003 | 7/1978 | Ashmead | 424/177 |
| 4,167,564 | 9/1979 | Jensen | 424/177 |
| 4,216,142 | 8/1980 | Ali | 260/112.5 R |
| 4,665,158 | 5/1987 | Armanet et al. | 530/357 |
| 4,830,716 | 5/1989 | Ashmead | 204/72 |
| 4,874,893 | 10/1989 | Flork | 562/443 |
| 5,278,329 | 1/1994 | Anderson | 556/50 |

*Primary Examiner*—Porfirio Nazario-Gonzalez
*Attorney, Agent, or Firm*—Zarley,McKee,Thomte, Voorhees, & Sease

[57] ABSTRACT

The method and composition involves preparing a high yield of a metal amino acid complex visible as a source of highly bioavailable transition metal ions, highly bioavailable essential amino acid for a livestock animal is disclosed. The method involves preparing the metal amino acid complex from a protein starting material resulting product in high yield. The protein starting material is hydrolyzed to provide an amino acid hydrolyzate and thereafter a metal oxide corresponding to the desired metal for the metal amino complex is added to the amino acid hydrolyzate to react to form a high yield metal amino acid complex which is thereafter used to form a dose for supplementation of diet to assure adequate trace minerals and adequate essential amino acids in the diet of a livestock animal.

14 Claims, No Drawings

5,698,724

AMINO ACID METAL COMPLEXES USING HYDROLYZED PROTEIN AS THE AMINO ACID SOURCE AND METHODS RE SAME

BACKGROUND OF THE INVENTION

The importance of an adequate supply of trace minerals such as zinc, chromium, manganese, iron, cobalt and copper and of the essential amino acids in the diet of both animals and humans has long been recognized in the literature. Small amounts of trace minerals such as zinc, manganese and iron have also been documented as not only extremely important in dietary function, but for other reasons such as healthy skin, etc. It is common to feed animals such as domestic livestock feed supplements that contain both essential amino acids and trace minerals.

It is also heretofore known that simple free choice feeding of essential amino acids, and conventional inorganic water soluble salts of trace minerals is not the most efficient way for diet supplementation. This is true because neither the amino acid nor the trace minerals is in their most bioavailable form. As a result, much of the potential value of both the essential amino acid and the trace mineral is wasted.

As a result of the above knowledge, the common assignee of the present application has in the past synthesized and patented certain 1:1 complexes of zinc, chromium, manganese and iron. See for example U.S. Pat. Nos. 3,941,818; 3,925,433, 3,950,372; 4,021,569; 4,067,994. Each of the above patents relate to 1:1 complexes of alpha amino acids, preferably methionine and of transition metals including zinc, chromium, manganese and iron. The complexes shown provided and claimed in the above patents are described as 1:1 complex salts because 1:1 complexes are more water soluble, are more bioavailable, and are more efficiently metabolized to provide maximum effective body usage of both the transition metal and the amino acid. Such has been demonstrated from data provided in some of the earlier referred to patents of the common assignee.

Each of the above patents describes, prepares and claims racemic mixtures of the metal methionine complexed salts. That is to say, the resulting salt as described is a 1:1 complexed salt which contains, for example, within the metal methionine complex, methionine that is a racemic mixture of the D-form of methionine and the L-form of methionine. U.S. Pat. No. 5,278,329 issued Jan. 11, 1994 refers to pure L-form complexes.

The prior patents, and the synthesis processes described in them, are all predicated upon use of pure amino acid as the starting reactant to prepare the metal amino acid complex. While these perform satisfactorily for the end user to provide both the trace mineral and the essential amino acid in highly bioavailable form, the fact is that pure essential amino acids are very expensive starting materials. It would therefore be desirable to provide a process by which proteins containing a peptide linkage may be hydrolyzed to provide in high yield a pure amino acid hydrolyzate which could thereafter be used in the synthesis reaction. This would avoid the need to use expensive, pure amino acids. It is a primary objective of the present invention to fulfill this need.

Another objective of the present invention is to provide a process of preparing substantially pure metal amino acid complexes of the metals zinc, copper, manganese, iron, cobalt and chromium, using as a starting material a protein source such as fish meal or corn gluten which is subjected to acid hydrolysis, and thereafter reacted with a metal oxide of the desired trace mineral. This results in substantially pure high yield metal amino acid complexes.

The method of accomplishing each of these and other objectives of the invention will become apparent from the detailed description which follows.

SUMMARY OF THE INVENTION

This invention relates to a novel method and composition for trace mineral and essential amino acid supplementation of the diet of livestock. The method involves preparing in high yield a metal amino acid complex from a protein starting material.

A process has been developed for the hydrolysis of a protein to its constituent amino acids using the optimum amount of a mineral acid to produce efficient hydrolysis without the necessity to remove excess acid after completion of hydrolysis by distillation in case of hydrochloric acid or precipitation of calcium sulfate in case of sulfuric acid. The invention also involves the selection of the correct temperature and time limits to ensure complete hydrolysis of the protein to its constituent amino acids in the shortest possible time with minimum destruction of the heat labile amino acids, followed by utilization of the mineral acid remaining after complete hydrolysis of the protein to its constituent amino acids to form the metal salts required for the formation of the amino acid-metal element complexes, and, finally, adjustment of the pH of the solution of the amino acid-metal complexes to neutralize unwanted acid and to assure formation of stable 1:1 amino acid-metal complexes.

DETAILED DESCRIPTION OF THE INVENTION

In this invention, a novel process is described for acid hydrolysis of a protein to its constituent amino acids and subsequent formation of 1:1 amino acid-metal complexes.

Hydrolysis of proteins to their constituent amino acids can be achieved by using catalysts such as mineral acids, bases and protolytic enzymes. Although acid catalyzed hydrolysis appears to be the most efficient and cost effective method for obtaining amino acids from proteins, it suffers from several shortcomings, including the long heating time required for complete hydrolysis, decomposition of some heat labile amino acids (serine, threonine, and tyrosine), and difficulty in removing mineral acid after complete hydrolysis. Several patents have been issued in the past to address some of these shortcomings and to optimize conditions for acid hydrolysis.

In 1951, Pattee (U.S. Pat. No. 2,555,276) used a mixture of hydrochloric acid and sulfuric acid for the hydrolysis of "distillers' dry grains". The mixture was heated under reflux at atmospheric pressure for 2 hours and then in a closed kettle at about 130° C. for 4 hours. The filtered acid hydrolyzate was then subjected to vacuum distillation at a temperature of about 60° C. for the removal of hydrochloric acid. The concentrated hydrolyzate was neutralized to pH 7.0 with lime slurry to precipitate calcium sulfate. The precipitated calcium sulfate was removed by filtration, and the filtrate contained the calcium salts of the amino acids.

In 1953, Borkenhagen (U.S. Pat. No. 2,657,232) described a process for separating inorganic salts from amino acids produced by acid hydrolysis of proteins by using an anhydrous organic solvent-ammonia mixture. The protein was heated with a mixture of concentrated sulfuric acid and water at 120° C.–130° C. for two hours. The resulting mixture was adjusted to pH 6.5 with ammonia and evaporated to dryness. The residue was extracted with ammoniacal methyl alcohol and filtered. The filtrate was evaporated to dryness. The extraction was repeated four more times to produce a residue of the free amino acids.

Armanet and Giddey (U.S. Pat. No. 4,665,158 issued May 12, 1987) described a method for hydrolyzing protein materials by treating dehydrated proteins with gaseous hydrochloric acid without temperature control. The reaction temperature increased rapidly, reaching momentarily 150° C. The material was cooled, and additional gaseous hydrogen chloride was added. The residue was heated under reduced pressure to remove hydrochloric acid, and the residue was dissolved in water and neutralized with sodium hydroxide.

In 1987 Flork (U.S. Pat. No. 4,874,893) described an industrial process for the preparation of amino acids by hydrolysis of proteins in acid medium. Sulfuric acid (12N) was heated in a vat to 100° C., and the protein was added. Hydrolysis conditions were maintained for 4 hours at 12N by the addition of sufficient concentrated sulfuric acid and at a temperature of 100° C. The reaction was stopped by the addition of water. Acid was removed by the addition of slaked lime to a pH of 1–2. The mixture is poured in a settling tank and left overnight. The clear supernatant containing the sulfate salts of the amino acids is removed.

None of the above-described prior methods teach an optimized short time, high yield hydrolysis specifically tailored for use in making trace mineral/amino acid complexes.

In accordance with the new process feature of this invention, these substantially pure metal amino acid complexes are prepared in high yield, not from the expensive pure amino acid starting material, but from protein starting materials. As those skilled in the art know, proteins are a series of amino acids connected by peptide linkages. In accordance with the present process, an acid hydrolysis of the protein starting material occurs to provide an amino acid hydrolyzate.

The protein starting material may be casein, feather meal, peanut meal, poultry byproduct meal, sunflower meal, corn gluten meal, soybean meal, soy protein concentrate, dried yeast, blood meal, fish meal, meat and bone meal, and other protein meals of vegetable or animal origin. Preferably, one uses the commonly available feather meal and corn gluten. These contain a known profile of most of the important essential amino acids for use by poultry and livestock.

The process of the present invention was developed for the hydrolysis of proteins to its constituent amino acids using the optimum amount of a mineral acid and optimum temperature for complete hydrolysis and for its subsequent use in formation of trace mineral complexes. The optimum amount of mineral acid was found to be approximately twice the amount required to protonate the α-amino groups of the amino acids produced after complete hydrolysis of the proteins. The optimum concentration of acid was found to be about 6 Molar. This amount of acid was sufficient to produce complete hydrolysis of protein. After hydrolysis, the amount of acid remaining in the hydrolysate is just sufficient to react with the metal oxide to facilitate the formation of the 1:1 amino acid-metal complex. Importantly, limiting the amount of acid used for hydrolysis eliminated the necessity of the costly and time-consuming procedure to remove acid after completion of the reaction.

The time required for complete hydrolysis of the protein to its constituent amino acids depends on the temperature of the hydrolysis reaction. However, at high temperatures, the heat labile amino acids (serine, thoreonine, and tyrosine) rapidly degrade. Therefore, it is important that the correct temperature for acid hydrolysis is selected. The correct temperature is functionally described as that at which the reaction time is as short as possible, with minimum destruction of heat labile amino acids. Heating the mixture of mineral acid and protein source at a preferred 145° C.–155° C. and at a pressure of 50 psi resulted in complete hydrolysis within 1–2 hours with minimum loss of the heat labile amino acids. Generally, the temperature should be within the range of 140° C.–160° C., the pressure within the range of 40 psi to 80 psi, and the time for from about 1 hour to about 3.0 hours.

The product of hydrolysis is a clear dark brown solution that contains the mixture of amino acids in the 6M mineral acid used for hydrolysis. The amount of acid present is twice that required to protonate the alpha amino group of the amino acids. Approximately one molar equivalent of metal oxide is typically added. This resulted in the initial formation of the mineral acid salt of the metal followed by the formation of the 1:1 complex of amino acid-metal. The addition of the metal oxide results in raising the pH of the solution to approximately 2. The addition of approximately one equivalent of an alkaline metal hydroxide such as sodium or potassium hydroxide results in raising the pH of the solution to approximately 4–5. At this pH range, the 1:1 complexes of the amino acid-trace element are most stable.

After the hydrolysis, as above described, conversion to pure amino acid, consistent with the amino acid profile of the starting materials, is generally at a high rate, often 90% or higher conversion. In some instances, the conversion is almost 100%.

After the hydrolysis has been completed, the metal amino acid complex of the desired metal is thereafter formed. The typical metal oxides used are zinc, copper, manganese, iron, cobalt and chromium. The complexes are formed directly in situ in the amino acid hydrolyzate by simply adding the corresponding metal oxide for the desired metal for the trace mineral of choice. This results in formation of the metal amino acid complexes in a proportion consistent with the profile of amino acid moieties in the starting protein meal material. In the final step, the pH is raised from acid, normally at about 1, to a pH of from about 4 to 5 by adding an alkali or an alkaline earth hydroxide material, typically sodium hydroxide.

The final material, particularly if it is a hygroscopic metal amino acid complex salt of an acid such as hydrochloric acid, is usually liquid. These syrup like liquids are so highly hydroscopic and they cannot be dried. It is therefore necessary to use a suitable carrier. Suitable carriers can be, for example, corncob flour, wood flour or other highly absorbent substantially inert carrier materials, like maltodextrin.

The following examples are offered to further illustrate the formation of substantially pure 1:1 metal amino acid complexes of zinc, copper, manganese, iron, cobalt and chromium from protein starting materials and the corresponding metal oxide by a hydrolyzing process.

EXAMPLE 1

Acid Hydrolysis of Corn Gluten Meal in Order to Obtain Optimum Yields of Free Amino Acid Conventional Acid Hydrolysis A 50 mg aliquot in 6 ml of 6M HCl (see Table 1), and a 100 mg aliquot in 3 ml of 6M HCl (see Table 2), were placed in 20 ml glass ampules, purged with nitrogen and vacuum sealed. These were then placed in an oven and hydrolyzed at 107°–110° C. for 24 hours. The residual acid was removed under vacuum with a rotovapor at 45°–50° C. The residue was thoroughly extracted with 20 ml of sodium citrate buffer (pH 2.2) and then centrifuged for approximately 10 minutes and the supernatant was saved and was further diluted with buffer for analysis. These and other samples from various trials were analyzed for amino acid composition with a Beckman 6300 amino acid analyzer. The analytical data is presented as grams of amino acids yield per 100 grams of corn gluten meal. The above conventional method gave an average of 63 g of free amino acids per 100 g sample. For our purposes, yields of amino acids over 60 g per 100 g sample will be considered 100% yields.

TABLE I g Amino Acids Per 100 g Sample
50 mg Aliquot in 6 ml 6 M HCl

| Amino Acid | Sample #1 | Sample #2 | Sample #3 |
|---|---|---|---|
| ASPARTIC ACID | 3.86 | 3.59 | 3.48 |
| THREONINE | 1.93 | 1.79 | 1.75 |
| SERINE | 2.77 | 2.55 | 2.48 |
| GLUTAMIC ACID | 13.62 | 12.81 | 12.41 |
| PROLINE | 5.92 | 5.56 | 5.33 |
| GLYCINE | 1.62 | 1.53 | 1.49 |
| ALANINE | 5.55 | 5.22 | 5.11 |
| VALINE | 3.11 | 2.91 | 2.84 |
| METHIONINE | 1.26 | 1.2 | 1.16 |
| ISOLEUCINE | 2.57 | 2.43 | 2.37 |
| LEUCINE | 10.53 | 9.94 | 9.75 |
| TYROSINE | 2.94 | 2.8 | 2.72 |
| PHENYLALANINE | 3.88 | 3.68 | 3.6 |
| LYSINE | 1.08 | 1.05 | 1.04 |
| HISTIDINE | 1.35 | 1.16 | 1.13 |
| ARGININE | 2.29 | 2.21 | 2.14 |
| Total | 64.28 | 60.43 | 58.80 |
| Average | 61.17 | | |

TABLE II

G Amino Acids Per 100 g Sample
100 mg Aliquot in 3 ml 6 M HCl

| Amino Acid | Sample #1 | Sample #2 | Sample #3 |
|---|---|---|---|
| ASPARTIC ACID | 3.57 | 3.61 | 3.51 |

TABLE II-continued

G Amino Acids Per 100 g Sample
100 mg Aliquot in 3 ml 6 M HCl

| Amino Acid | Sample #1 | Sample #2 | Sample #3 |
|---|---|---|---|
| THREONINE | 1.78 | 1.83 | 1.78 |
| SERINE | 2.53 | 2.65 | 2.58 |
| GLUTAMIC ACID | 12.6 | 12.95 | 12.51 |
| PROLINE | 5.4 | 5.59 | 5.39 |
| GLYCINE | 1.54 | 1.58 | 1.53 |
| ALANINE | 5.69 | 5.83 | 5.64 |
| VALINE | 2.85 | 2.95 | 2.83 |
| METHIONINE | 1.07 | 1.14 | 1.08 |
| ISOLEUCINE | 2.43 | 2.53 | 2.43 |
| LEUCINE | 10.04 | 10.4 | 10.08 |
| TYROSINE | 2.27 | 2.43 | 2.29 |
| PHENYLALANINE | 3.7 | 3.87 | 3.75 |
| LYSINE | 0.92 | 0.97 | 0.94 |
| HISTIDINE | 1.08 | 1.16 | 1.14 |
| ARGININE | 1.7 | 1.77 | 1.71 |
| Total | 59.17 | 61.26 | 59.19 |
| Average | 59.87 | | |

A determination was made of the minimal quantity of hydrochloric acid needed to complete the hydrolysis in the following manner. Using the conventional method above described, the amount of HCL was varied to determine the minimal amount needed to achieve 100% yield. 100 mg samples were used; otherwise the procedures are the same as mentioned above. Amounts of HCl used were: 3 ml, 1.5 ml, 1.0 ml, 0.5 ml, 0.25 ml, 0.2 ml, 0.15 ml, and 0.1 ml. As seen, one could achieve 100 percent yields using as little as 0.15 ml HCL per 100 mg sample. 0.1 ml HCL achieved approximately 87% yields. (See Table III).

TABLE III g Amino Acids Per 100 g Sample

| Amino Acid | 3.0 ml HCl | 1.5 ml HCl | 1.0 ml HCl | 0.5 ml HCl | 0.25 m 1 HCl | 0.20 m 1 HCl | 0.15 m 1 HCl | 0.10 m 1 HCl |
|---|---|---|---|---|---|---|---|---|
| ASPARTIC ACID | 3.61 | 3.68 | 3.87 | 3.6 | 3.68 | 3.72 | 3.6 | 3.37 |
| THREONINE | 1.77 | 1.82 | 1.74 | 1.77 | 1.74 | 1.66 | 1.6 | 1.43 |
| SERINE | 2.45 | 2.54 | 2.14 | 2.52 | 2.44 | 2.25 | 2.23 | 2.2 |
| GLUTAMIC ACID | 12.88 | 13.09 | 12.94 | 12.81 | 12.56 | 12.72 | 12.33 | 10.62 |
| PROLINE | 5.6 | 5.6 | 5.76 | 5.48 | 5.51 | 5.63 | 5.5 | 5.23 |
| GLYCINE | 1.53 | 1.56 | 1.59 | 1.52 | 1.54 | 1.58 | 1.55 | 1.45 |
| ALANINE | 5.31 | 5.38 | 5.59 | 5.3 | 5.44 | 6.03 | 5.97 | 5.7 |
| VALINE | 2.99 | 2.99 | 3.03 | 2.9 | 2.86 | 2.87 | 2.74 | 2.38 |
| METHIONINE | 1.15 | 1.13 | 1.14 | 1.07 | 1.02 | 1 | 0.95 | 0.93 |
| ISOLEUCINE | 2.55 | 2.53 | 2.62 | 2.43 | 2.39 | 2.49 | 2.38 | 1.69 |
| LEUCINE | 10.36 | 10.26 | 10.66 | 10.08 | 10.12 | 10.52 | 10.28 | 9.02 |
| TYROSINE | 2.38 | 2.13 | 2.03 | 1.76 | 1.66 | 1.63 | 1.61 | 1.56 |
| PHENYLALANINE | 3.83 | 3.79 | 3.86 | 3.73 | 3.73 | 3.8 | 3.7 | 3.2 |
| LYSINE | 1.08 | 1.06 | 1.11 | 1.04 | 1.05 | 1.09 | 1.07 | 0.9 |
| HISTIDINE | 1.16 | 1.18 | 1.03 | 1.16 | 1.16 | 1 | 0.97 | 0.97 |
| ARGININE | 2.14 | 2.26 | 2.56 | 2.11 | 2.07 | 2.53 | 2.35 | 1.82 |
| Total | 60.79 | 61.0 | 61.67 | 59.29 | 58.97 | 60.52 | 58.83 | 52.47 |

EXAMPLE 2

Acid Hydrolysis of Feather Meal in Order to Obtain Optimum Yields of Free Amino Acids For comparison purposes a conventional acid hydrolysis was conducted with feather meal.

100 mg aliquots in 6 ml of 6M HCl were placed in 20 ml glass ampules, purged with nitrogen and vacuum sealed. These were then placed in an oven and hydrolyzed at 107°–110° C. for 24 hours. The residual acid was removed under vacuum with a rotovapor at 45°–50° C. The residue was thoroughly extracted with 20 ml of sodium citrate buffer (pH 2.2) and then centrifuged for approximately 10 minutes, and the supernatant was saved and was further diluted with buffer for analysis. These and other samples from various trials were analyzed for amino acid composition with a Beckman 6300 amino acid analyzer. The above conventional method gave an average of 68–69 g of free amino acids per 100 g sample. For our purposes, yields of antino acids over 68 g per 100 g sample will be considered 100% yields (see Table 4). There was no significant difference in yield of amino acids, whether one used redistilled 6M HCl or the reagent grade 6M HCl; therefore, in all subsequent trials 6M reagent grade hydrochloric acid was used.

TABLE IV

| Amino Acid | g Amino Acids Per 100 g Sample | | | | |
|---|---|---|---|---|---|
| | Exp #1 | Exp #2 | Exp #3 | Exp #4 | Exp #5 |
| ASPARTIC ACID | 5.18 | 5.21 | 5.32 | 5.01 | 5.33 |
| THREONINE | 3.07 | 3.13 | 3.31 | 2.95 | 3.18 |
| SERINE | 5.35 | 5.55 | 6.73 | 5.21 | 5.91 |
| GLUTAMIC ACID | 7.56 | 7.68 | 8.21 | 7.31 | 7.84 |
| PROLINE | 7.18 | 7.31 | 7.66 | 6.88 | 7.34 |
| GLYCINE | 5.92 | 6.05 | 6.29 | 5.70 | 6.15 |
| ALANINE | 3.48 | 3.65 | 3.72 | 3.48 | 3.71 |
| VALINE | 6.16 | 6.17 | 6.13 | 5.89 | 6.17 |
| METHIONINE | 0.77 | 0.78 | 0.77 | 0.76 | 0.79 |
| ISOLEUCINE | 3.61 | 3.64 | 3.59 | 3.45 | 3.64 |
| LEUCINE | 6.1 | 6.17 | 6.26 | 5.95 | 6.25 |
| TYROSINE | 1.84 | 1.88 | 2.01 | 1.83 | 1.96 |
| PHENYLALANINE | 3.55 | 3.59 | 3.67 | 3.46 | 3.64 |
| LYSINE | 2.12 | 2.17 | 2.32 | 2.13 | 2.31 |
| HISTIDINE | 0.76 | 0.78 | 0.77 | 0.80 | 0.87 |
| ARGININE | 4.79 | 4.98 | 5.35 | 4.74 | 5.15 |
| Total | 67.44 | 68.74 | 72.11 | 65.55 | 70.24 |
| Average | 68.81 | | | | |

For this example a determination of minimal quantity of hydrochloric acid needed to complete the hydrolysis was also conducted. Using the conventional method, the amount of HCl was varied to determine the minimal amount needed to achieve 100% yield. 100 mg samples were used; otherwise procedures are the same as mentioned above. Amounts of HCl used were: 1 ml, 0.5 ml, 0.4 ml, 0.3 ml, and 0.2 ml. As seen, one could achieve 100 percent yields using as little as 0.20 ml HCL per 100 mg sample. See Table V.

TABLE V

| Amino Acid | g Amino Acids Per 100 g Sample | | | | |
|---|---|---|---|---|---|
| | 1.0 ml HCl | 0.5 ml HCl | 0.4 ml HCl | 0.3 ml HCl | 0.2 ml HCl |
| ASPARTIC ACID | 5.18 | 5.4 | 5.17 | 5.15 | 5.13 |
| THREONINE | 3.09 | 3.17 | 3.16 | 3.1 | 3.14 |
| SERINE | 5.97 | 6.29 | 6.45 | 6.56 | 6.77 |
| GLUTAMIC ACID | 7.74 | 8.14 | 7.97 | 8 | 7.89 |
| PROLINE | 7.15 | 7.33 | 7.18 | 7.29 | 7.36 |
| GLYCINE | 6.01 | 6.15 | 6 | 6.04 | 6.14 |
| ALANINE | 3.62 | 3.87 | 3.71 | 3.84 | 3.75 |
| VALINE | 5.9 | 6.06 | 5.73 | 5.62 | 5.6 |
| METHIONINE | 0.72 | 0.79 | 0.81 | 0.8 | 0.8 |
| ISOLEUCINE | 3.47 | 3.54 | 3.43 | 3.44 | 3.39 |
| LEUCINE | 6.13 | 6.39 | 6.19 | 6.14 | 6.14 |
| TYROSINE | 1.45 | 1.35 | 1.39 | 1.45 | 1.47 |
| PHENYLALANINE | 3.57 | 3.69 | 3.57 | 3.58 | 3.67 |
| LYSINE | 2.2 | 2.36 | 3.29 | 2.17 | 2.26 |
| HISTIDINE | 0.81 | 0.82 | 0.87 | 0.86 | 0.84 |
| ARGININE | 4.9 | 5.06 | 4.96 | 4.92 | 5.04 |
| Total | 67.91 | 70.41 | 69.88 | 68.96 | 69.39 |

A time dependency study was made on the hydrolysis for this example. In particular, using the conventional long hydrolysis method, 100 mg aliquots were prepared in 3 ml of 6M HCl and hydrolyzed for 12 hours, 24 hours and 48 hours. The latter two each produced 100% yields (see Table 6). The 12 hour hydrolysate gave almost 100% yields of all the amino acids when compared to the 24 and 48 hour hydrolysates. Therefore, it was demonstrated that feather meal may be hydrolyzed overnight using the conventional method and produce yields equal to that of 24 or 48 hour hydrolysis.

TABLE VI

| Amino Acid | g Amino Acids Per 100 g Sample | | | | | |
|---|---|---|---|---|---|---|
| | 12 Hours | 12 Hours | 24 Hours | 24 Hours | 48 Hours | 48 Hours |
| ASPARTIC ACID | 5.33 | 5.5 | 5.26 | 5.56 | 5.58 | 5.57 |
| THREONINE | 3.43 | 3.64 | 3.13 | 3.29 | 2.98 | 2.97 |
| SERINE | 6.83 | 8.11 | 5.7 | 5.91 | 5 | 4.97 |
| GLUTAMIC ACID | 8.11 | 8.73 | 7.99 | 8.31 | 8.62 | 8.45 |
| PROLINE | 7.29 | 7.71 | 7.28 | 7.54 | 7.91 | 7.6 |
| GLYCINE | 6.27 | 6.49 | 6.24 | 6.47 | 6.59 | 6.36 |
| ALANINE | 3.6 | 3.83 | 3.69 | 3.89 | 3.93 | 3.88 |
| VALINE | 5.96 | 6.01 | 6.34 | 6.68 | 6.69 | 6.54 |
| METHIONINE | 0.7 | 0.77 | 0.73 | 0.75 | 0.7 | 0.7 |
| ISOLEUCINE | 3.55 | 3.6 | 3.61 | 3.8 | 3.68 | 3.58 |
| LEUCINE | 6.2 | 6.3 | 6.1 | 6.4 | 6.4 | 6.34 |
| TYROSINE | 2.03 | 2.15 | 1.67 | 1.71 | 1.12 | 1.17 |

TABLE VI-continued

| | g Amino Acids Per 100 g Sample | | | | | |
|---|---|---|---|---|---|---|
| Amino Acid | 12 Hours | 12 Hours | 24 Hours | 24 Hours | 48 Hours | 48 Hours |
| PHENYLALANINE | 3.6 | 3.7 | 3.56 | 3.74 | 3.74 | 3.7 |
| LYSINE | 2.17 | 2.2 | 2.15 | 2.23 | 2.34 | 2.45 |
| HISTIDINE | 0.82 | 0.78 | 0.69 | 0.81 | 0.73 | 0.84 |
| ARGININE | 5.28 | 5.56 | 5.09 | 5.23 | 5.33 | 5.19 |
| Total | 71.17 | 75.08 | 69.23 | 72.32 | 71.34 | 70.31 |

The temperature dependency of the hydrolysis was also studied. In particular, using the conventional method, three 100 mg aliquots were prepared using 1.5 ml of 6M HCl and placed in an oven at various temperatures for various lengths of time. The first was hydrolyzed at 160° C. for two hours and gave a 90% yield, but there was almost a complete breakdown of threonine and serine. The second sample was hydrolyzed at 150° C. for three hours giving an 85% yield. Again, there was almost a total breakdown of threonine, serine and also tyrosine. The third sample hydrolyzed was done at 140°–145° C. for 4 hours and produced a 100% yield with no substantial breakdown of any of the amino acids (See Table VII).

TABLE VII

| | g Amino Acids Per 100 g Sample | | |
|---|---|---|---|
| Amino Acid | 160 C. 2 hours | 150 C. 3 hours | 140–145 C. 4 hours |
| ASPARTIC ACID | 5.04 | 4.8 | 5.41 |
| THREONINE | 0.82 | 0.63 | 2.53 |
| SERINE | 0.41 | 0.22 | 4.06 |
| GLUTAMIC ACID | 8.45 | 7.97 | 8.8 |
| PROLINE | 7.9 | 7.56 | 8.15 |
| GLYCINE | 6.36 | 6.09 | 6.49 |
| ALANINE | 4.42 | 4.26 | 3.96 |
| VALINE | 6.39 | 6.04 | 6.52 |
| METHIONINE | 0.49 | 0.46 | 0.61 |
| ISOLEUCINE | 2.97 | 2.68 | 3.44 |
| LEUCINE | 6.03 | 5.76 | 6.28 |
| TYROSINE | 0.44 | 0.47 | 1.15 |
| PHENYLALANINE | 3.52 | 3.34 | 3.66 |
| LYSINE | 2.35 | 2.23 | 2.33 |
| HISTIDINE | 0.7 | 0.66 | 0.76 |
| ARGININE | 4.4 | 4.21 | 5.2 |
| Total | 60.69 | 57.38 | 69.35 |

EXAMPLE 3

Feather Meal Hydrolysis Example, Samples 1, 2 and 3

A reactor vessel used in the hydrolysis of the protein into amino acids was A DeDiedrich, Inc. model CTJ-32-100 glass lined steel clamp top jacketed reactor vessel.

Approximately 103 pounds of water was added to the vessel followed by 240 pounds of 31.4% HCl to make 343 pounds of 6N hydrochloric acid. To this was added 150 pounds of feather meal (80% guaranteed crude protein). The final weight of the mixture was, therefore, 493 pounds, of which the feather meal made up 30.4% by weight. At this stage the physical appearance of the mixture was a thick, tan/light brown colored slurry. Agitation was begun after the feather meal had been added. The vessel was sealed and a vacuum was drawn using a vacuum pump. After a vacuum of 26 inches of mercury had been drawn, the vessel was purged with nitrogen. A vacuum of 26 inches of mercury was then drawn for a second time, at which time heating was begun by use of the vessel's steam jacket. Steam was provided at 85 psi to the vessel's steam jacket. After approximately 60 minutes the contents of the vessel had reached a temperature of 130° C. The vessel had developed approximately 50 psi of pressure due to the heating of its contents. As soon as the temperature inside the vessel had reached 130° C., a sample of the contents (about 200 ml) was carefully taken by partly opening a valve on the vessel. The sample liquid was a dark brown solution which appeared to be uniform in nature with little or no precipitate. The solution was much less viscous than at the beginning of the experiment. This sample #1 was sent to Woodson Tenent Laboratories in Des Moines, Iowa for free amino acid analysis (see Table 8).

The vessel was sealed again, and heating was resumed until the contents had reached 140° C. As soon as the temperature inside the vessel had reached 140° C., a sample of the contents (about 200 ml) was carefully taken by partly opening a valve on the vessel. Again, the solution was unchanged in appearance from the earlier sample. This sample #2 was also sent to Woodson Tenent Laboratories in Des Moines, Iowa for free amino acid analysis (see Table 8). The vessel was sealed again, and heating was resumed so that the 140° C. temperature could be maintained for one additional hour. The heating was stopped at the end of one hour. A sample of the contents (about 200 ml) was again carefully taken. The sample was still unchanged in its physical appearance from the previous two samples. This sample #3 was also sent to Woodson Tenent Laboratories in Des Moines, Iowa for free amino acid analysis (see Table VIII).

The vessel was slowly opened and the pressure released. After approximately 1 hour of venting, the contents of the vessel had cooled to about 90° C. and the pressure had been reduced to 0 psi.

The results of this experiment were as follows:

TABLE VIII

| | Amino Acid Analysis of Feather Meal Samples | | | |
|---|---|---|---|---|
| Amino Acid | Control | Sample 1 130 Deg. 0 hr. | Sample 2 140 Deg. 0 hr. | Sample 3 140 Deg. 1 hr. |
| ASPARTIC ACID | 5.55 | 2.55 | 3.54 | 4.12 |
| THREONINE | 4.14 | 2.72 | 3.57 | 3.62 |
| SERINE | 10.04 | 7.57 | 8.49 | 8 |
| GLUTAMIC ACID | 9.52 | 4.93 | 7.04 | 8.41 |
| PROLINE | 8.05 | 5.71 | 7.28 | 7.36 |
| GLYCINE | 6.34 | 6 | 6.72 | 6.93 |
| ALANINE | 3.62 | 3.39 | 3.97 | 4.38 |

TABLE VIII-continued

Amino Acid Analysis of Feather Meal Samples

| Amino Acid | Control | Sample 1 130 Deg. 0 hr. | Sample 2 140 Deg. 0 hr. | Sample 3 140 Deg. 1 hr. |
|---|---|---|---|---|
| VALINE | 5.39 | 3.01 | 4.7 | 5.83 |
| METHIONINE | 0.73 | 0.96 | 0.75 | 0.78 |
| ISOLEUCINE | 3.62 | 2.09 | 3.42 | 3.86 |
| LEUCINE | 6.5 | 4.58 | 6.26 | 6.81 |
| TYROSINE | 2.31 | 1.74 | 2.09 | 1.91 |
| PHENYLALANINE | 3.88 | 2.84 | 3.71 | 3.88 |
| HISTIDINE | 1.04 | 1.77 | 1.28 | 1.16 |
| LYSINE | 1.73 | 1.1 | 1.54 | 1.71 |
| ARGININE | 6.15 | 3.3 | 4.78 | 5.51 |
| Total | 78.61 | 54.26 | 69.14 | 74.27 |
| Yield % | 100.0% | 69.0% | 88.0% | 94.5% |

From this example it is clear that the protein source was not completely hydrolyzed in samples #1 and #2. Sample #3 showed a high degree of hydrolysis had been achieved.

EXAMPLE 4

(Degree of Hydrolysis)

Because of the high degree of hydrolysis achieved in the previous example on sample #3, (140° C. for 1 hour), a second set of experiments was conducted to evaluate the degree of hydrolysis that could be achieved using the 140° for one hour set of conditions. The same procedures were followed in this set of experiments as were outlined in the prior experiments. In this set of experiments, however, a sample was taken at 1 hour after 140° C. had been reached and again at each subsequent hour up to and including six hours after having reached and maintained 140° C. The results of these experiments are as follows:

TABLE IX g Amino Acids Per 100 g Sample

| Amino Acid | Control | 1 hr. | 2 hr. | 3 hr. | 4 hr. | 5 hr. | 6 hr. |
|---|---|---|---|---|---|---|---|
| ASPARTIC ACID | 5.52 | 5.54 | 5.68 | 4.99 | 6.09 | 6.2 | 6.03 |
| THREONINE | 4.01 | 3.71 | 3.57 | 2.99 | 3.28 | 3.16 | 2.87 |
| SERINE | 9.75 | 9.01 | 8.26 | 6.58 | 6.99 | 6.41 | 5.59 |
| GLUTAMIC ACID | 9.94 | 9.86 | 9.86 | 8.84 | 10.58 | 10.9 | 10.64 |
| PROLINE | 8.29 | 10 | 10 | 8.35 | 10 | 9.74 | 10.23 |
| GLYCINE | 7.45 | 7.3 | 7.39 | 6.58 | 7.77 | 8.14 | 7.91 |
| ALANINE | 4.38 | 4.64 | 5.07 | 4.67 | 5.94 | 6.64 | 6.64 |
| VALINE | 6.24 | 6.23 | 6.72 | 6.2 | 7.48 | 7.94 | 7.74 |
| METHIONINE | 0.62 | 0.72 | 0.67 | 0.58 | 0.55 | 0.55 | 0.61 |
| ISOLEUCINE | 3.97 | 4 | 4.23 | 3.8 | 4.41 | 4.58 | 4.55 |
| LEUCINE | 6.67 | 7.04 | 7.28 | 6.46 | 7.71 | 7.94 | 7.77 |
| TYROSINE | 2.3 | 2.06 | 1.77 | 1.3 | 1.33 | 1.1 | 0.93 |
| PHENYLALANINE | 3.96 | 4.09 | 4.23 | 3.77 | 4.64 | 4.61 | 4.49 |
| HISTIDINE | 0.95 | 1.1 | 1.16 | 1.1 | 1.33 | 1.39 | 1.39 |
| LYSINE | 1.68 | 1.77 | 1.83 | 1.74 | 2.03 | 2.12 | 2.09 |
| ARGININE | 5.58 | 5.68 | 5.86 | 5.25 | 6.2 | 6.2 | 5.97 |
| Total | 81.31 | 82.75 | 83.58 | 73.2 | 86.33 | 87.62 | 85.45 |
| Yield % | 100.0% | 101.8% | 102.8% | 90.0% | 106.2% | 107.8% | 105.1% |

This set of experiments confirmed that complete hydrolysis can be achieved by heating the contents to 140° C. and maintaining that temperature for one hour. The experiments using longer periods of time, while not as efficient from the standpoint of time, also worked well in producing complete hydrolysis and little or no amino acid degradation. The lower yield shown at 3 hours seems to be related to analytical or sampling error rather than actual lowered yield because the following yields at times 4 hours through 6 hours were again 100%. It is important to remember that all six samples were taken from the same original batch of protein. The only variable was the length of time it had been maintained at 140° C.

The next stage in producing metal amino acid complexes is to take amino acid mixtures obtained through the process described in the previous set of experiments and complex them with metal ions such as zinc, manganese, copper, iron, and chromium. The following set of experiments were conducted to evaluate the effectiveness of such complexing.

EXAMPLE 5

Zinc Amino Acid Complexes from Feather Meal

A reaction vessel as described in the prior experiments was loaded with 103 pounds of water and 240 pounds of 31.4% hydrochloric acid. To this acid solution was added 150 pounds of feather meal. The feather meal was hydrolyzed according to the process described in example 4. After the contents had been heated to 140° C. and maintained at that temperature for one hour, the heating was stopped and a sample of liquid was taken and appeared to be similar to the dark brown liquids described in the prior experiments. The vessel was then allowed to cool and depressurize. At this stage, while continuing to provide agitation, 84 pounds of a commercially available zinc oxide powder (80% Zn) was introduced into the vessel. After the addition, the contents were allowed to mix for approximately 20 minutes. A second sample of the contents was taken and observed. There appeared to be virtually no undissolved zinc oxide powder remaining. The hydrochloric acid present in the vessel had reacted with the zinc oxide to form zinc chloride. The pH of the solution was approximately 2.5 at this stage. Sodium hydroxide solution 50% w/w was added stepwise to the mixture, and the pH was measured at each step. The following table outlines the amounts of sodium hydroxide solution added and the corresponding pH. No precipitate was observed to have been formed by the addition of the sodium hydroxide solution. To this final solution was added 330 pounds each of maltodextrin and water. Maltodextrin is a water soluble carrier suitable for drying in a conventional spray drier. The product dried to a fine brown powder that analyzed 10.31% zinc.

TABLE X

| Pounds of Sodium Hydroxide Solution Added (50% w/w) | Measured pH of Zinc Amino Acid Solution |
| --- | --- |
| 0 | 3.3 |
| 15 | 3.9 |
| 20 | 4.1 |
| 25 | 4.4 |
| 30 | 4.6 |
| 35 | 4.9 |

EXAMPLE 6

Copper Amino Acid Complexes

In the same manner as described in the zinc complexing experiment, a copper amino acid product was produced. 240 pounds of 31.4% hydrochloric acid was added to 103 pounds of water. To this was added 150 pounds of feather meal. After hydrolysis and cooling according to the previously described method, 83 pounds of a commercially available copper oxide product (75% Cu) was added to the mixture and allowed to mix for approximately 20 minutes. A sample of the liquid showed no undissolved copper oxide powder remaining in the liquid. The pH of this liquid was measured to be approximately 1.0. Sodium hydroxide solution (50% w/w) was added stepwise to the liquid and the pH measured at each step. The following table outlines the amounts of sodium hydroxide solution added and the corresponding pH. To the final solution was added 270 pounds of both water and maltodextrin. The solution was dried in a spray drier. The finished product was dark brown in appearance and analyzed at approximately 10.3% copper.

TABLE XI

| Pounds of NaOH solution added (50% w/w) | Measured pH of copper amino acid solution |
| --- | --- |
| 0 | 1.0 |
| 25 | 1.9 |
| 38 | 2.9 |
| 56 | 3.4 |
| 65 | 4.1 |
| 75 | 4.5 |

EXAMPLE 7

Manganese Amino Acid Complexes

Two techniques were used to produce manganese amino acid complexes. First, in the manner described in both the zinc and copper complexing examples, a manganese oxide (MnO) product was utilized.

In the same reaction vessel described above, 240 pounds of 31.4% hydrochloric acid was added to 103 pounds water. Next, 150 pounds of feather meal was utilized and hydrolyzed according to the previously described method. After hydrolysis and cooling, 73 pounds of manganese oxide powder (77% Mn) was added to the mixture. This was allowed to mix for an additional 20 minutes. A sample of the liquid was then taken and showed that not all of the MnO had dissolved. It became necessary to add an additional 50 pounds of 31.4% hydrochloric acid to the vessel in order to get the MnO to completely dissolve. The pH of this solution was below 1.0 at this time. After adding 40 pounds of 50% w/w sodium hydroxide solution, the pH had risen to approximately 4.6. To this solution was added 335 pounds of both maltodextrin and water. The finished, spray-dried product was dark brown in color and analyzed at 8.25% manganese.

EXAMPLE 8

Manganese Amino Acid Complexes

The second method of producing manganese amino acid complexes utilized was as follows: 150 pounds of feather meal was hydrolyzed in the previously described method using 240 pounds of 31.4% hydrochloric acid and 103 pounds of water. To this amino acid solution was added 197 pounds of water and 200 pounds of a commercially available manganese sulfate powder containing 32% Mn. After all the manganese sulfate had been added, the solution was allowed to mix for an additional 20 minutes. 165 pounds of sodium hydroxide solution (50% w/w) was added slowly. The pH of the final solution was approximately 4.5, and there appeared to be no precipitate formed. 507 pounds of both maltodextrin and water were added to the solution and spray dried. The finished product was a brown powder that upon analysis contained approximately 6.2% manganese.

EXAMPLE 9

Iron Amino Acid Complexes

In the same manner of the second manganese example described above, an iron amino acid complex product was formed as follows: A reaction vessel as described in the prior experiments was loaded with 103 pounds of water and 240 pounds of 31.4% hydrochloric acid. To this acid solution was added 150 pounds of feather meal. The feather meal was hydrolyzed according to the process described in example 4. After the contents had been heated to 140° C. and maintained at that temperature for one hour, the heating was stopped and the vessel allowed to cool and vent. A sample of liquid was taken and appeared to be similar to the dark brown liquids described in the prior experiments. At this stage, while continuing to provide agitation, 193 pounds of a commercially available ferrous sulfate powder (30% Fe) was added to the mixture. After all the ferrous sulfate powder had been added, the contents of the vessel were allowed to mix for an additional 20 minutes. Next, 165 pounds of sodium hydroxide solution (50% w/w) was added slowly. The pH of the final solution was approximately 4.2 and there appeared to be no precipitate formed. 419 pounds of both maltodextrin and water were added to the solution and spray dried. The finished product was a brown powder that upon analysis contained approximately 6.2% iron.

EXAMPLE 10

Combination Zinc, Copper and Manganese Amino Acid Complexes

A single product containing several metal amino acid complexes may have commercial interest, and so two experiments were conducted to evaluate the production of zinc, copper and manganese amino acid complexes in a single production process. The first experiment was conducted as follows: A reaction vessel as described in the prior experiments was loaded with 159 pounds of water and 372 pounds of 31.4% hydrochloric acid. To this acid solution was added 233 pounds of feather meal. The feather meal was hydrolyzed according to the process described in example 4.

15

After the contents had been heated to 140° C. and maintained at that temperature for one hour, the heating was stopped and a sample of liquid was taken and appeared to be similar to the dark brown liquids described in the prior experiments. The vessel was then allowed to cool and vent. At this stage, while continuing to provide agitation, 67 pounds of zinc oxide (80% Zn) was added and allowed to dissolve. Next, 25 pounds of copper oxide (75% Cu) was added and allowed to dissolve. Next, 93 pounds of manganese sulfate was added and allowed to dissolve. Finally, 140 pounds of 50% w/w sodium hydroxide was added and the final pH was about 4.3. No precipitate or undissolved minerals were present in the final liquid. To this final liquid was added 329 pounds of both maltodextrin and water. The spray dried finished product was brown in color and analyzed as follows: Zn 2.69%, Cu 0.94%, Mn 1.49%.

EXAMPLE 11

Combination Zinc, Copper and Manganese Amino Acid Complexes

The second method used to produce a combination metal amino acid complex product was as follows: A reaction vessel as described in the prior experiments was loaded with 176 pounds of water and 410 pounds of 31.4% hydrochloric acid. To this acid solution was added 240 pounds of feather meal. The feather meal was hydrolyzed according to the process described in example 4. After the contents had been heated to 140° C. and maintained at that temperature for one hour, the heating was stopped and a sample of liquid was taken and appeared to be similar to the dark brown liquids described in the prior experiments. The vessel was then allowed to cool and vent. At this stage, while continuing to provide agitation, 67 pounds of zinc oxide (80% Zn) was added and allowed to dissolve. Next, 25 pounds of copper oxide (75% Cu) was added and allowed to dissolve. Next, 38 pounds of manganese oxide (77% Mn) was added and allowed to dissolve. Finally, 84 pounds of 50% w/w sodium hydroxide was added and the final pH was about 4.1. No precipitate or undissolved minerals were present in the final liquid. To this final liquid was added 444 pounds of both maltodextrin and water. The spray dried finished product was brown in color and analyzed as follows: Zn 5.30%, Cu 1.85%, Mn 2.89%.

EXAMPLE 12

(Pen Broiler Trials)

The purpose of the present tests was to evaluate the product of this invention in comparison with control and in comparison with product of assignee currently being sold which comprises amino acid metal complexes resulting from complexation between metal salts and pure amino acids.

Normal, healthy day-old chicks were obtained from a commercial hatchery. The birds were transported from the hatchery location to the test site via commercial air freight. Details concerning the birds were as follows:

| | |
|---|---|
| Species: | Chickens (*Gallus domesticus*) Commercial broilers (high yield cross) |
| Breed: | Arbor Acres × Arbor Acres |
| Source: | Arbor Acres Farms, Blairsville, GA |
| Age: | 0 day of age upon receipt |

16

-continued

| | ~53 days of age at final weights |
|---|---|
| Sex: | Male |
| Identification: | Pen cards |
| Number of birds/pen: | 75 started (reduced to 73 at 7 days of age) |
| Number of reps/treatment: | 10 |
| Total number of treatments: | 4 |
| Total number of pens: | 40 |
| Number of birds/treatment: | 750 started (730 at 7 days of age) |
| Total number of birds: | 3000 started (2920 at 7 days of age) |

The feed ration contained the following feed additives:

Sacox (30 g/lb premix; lot no. P5082005); fed at 60 g/ton in starter and grower diets.

Bacitracin MD (50 g/lb premix; lot no. BB140166); fed at 50 g/ton in starter diets; 25 g/ton in grower and finisher diets.

Roxarsone (90.8 g/lb premix; lot no. AB540250); fed at 45 g/ton in starter and grower diets.

The tests were conducted with Zinc Methionine (Zinpro 100); Zinc Methionine plus Zinc Lysine (Zinplex); and Control containing no zinc or amino acid complex; and finally the zinc amino acid complexes of the present invention prepared from hydrolyzed protein as the amino acid source.

Treatments were assigned to pens using a randomized block design. The research facility was divided into 10 blocks of 4 pens each. Birds were assigned to pens randomly. The specific treatment groups were as listed in Table XII.

TABLE XII

| Treatment | Test Article | Sacox at 60 g/ton in Starter and Grower Diets | Infect w/E. maxima | No. of Pens | No. of Birds/ Pen | Total No. of Birds |
|---|---|---|---|---|---|---|
| 1 | Control | Yes | Yes | 10 | 73 | 730 |
| 2 | Zinc methionine (Zinpro 100) | Yes | Yes | 10 | 73 | 730 |
| 3 | Zinc methionine + Zinc Lysine (Zinplex) | Yes | Yes | 10 | 73 | 730 |
| 4 | Invention | Yes | Yes | 10 | 73 | 730 |
| | TOTAL | | | 40 | | 2920 |

Birds were housed in concrete floor pens of an environmentally controlled facility. All birds were placed on used litter top-dressed with approximately 2 inches of clean wood shavings. Lighting followed a commercial program and has been documented in the study records.

Floor space was approximately 0.85 sq. feet per bird. Ventilation and heat were provided and adjusted as necessary to maintain bird comfort. These housing conditions simulated field conditions.

In order to prevent bird migration, each pen was checked to assure no openings greater than 1 inch existed for approximately 18 inches in height between pens. To achieve this a double-mesh poultry wire was in place for approximately the first 18 inches from the floor.

Birds were vaccinated for Mareks at the hatchery. The birds were vaccinated for Newcastle and Infectious Bronchitis via the drinking water at 7 days of age at the Investigator's facility. No other vaccinations or treatments, except the test article and feed additives indicated above, were administered during the study.

Water was provided ad libitum throughout the study via one hanging, ~14-inch diameter automatic bell drinker per pen. A floor-placed gallon drinker was also placed in each pen for approximately the first 5 days. Drinkers were checked twice daily and cleaned as needed to assure a clean water supply to birds at all times.

Feed was provided ad libitum throughout the study via two hanging, ~17-inch diameter tube feeders per pen. A chick feeder tray was also placed in each pen for approximately the first 7 days. All birds were placed on their respective treatment diets upon receipt from the hatchery. All feed added and removed from pens was weighed and recorded.

The test facility, pens and birds, were observed twice daily for general flock condition, lighting, water, feed, ventilation and unanticipated events. If abnormal conditions or abnormal behavior were noted at any of the twice daily observations, they were recorded as an unanticipated event and were noted on the "Unanticipated Events" record. At least once weekly the birds were observed for general health.

The minimum-maximum temperature of the test facility was recorded once daily. Observations and temperatures were recorded on the House Observation Record.

At 7 days of age the birds in each pen were counted, and the count was adjusted to 73 birds in each pen. All mortalities/removals from day 7 to study end were recorded and necropsied to determine probable cause of death. Birds unable to get to feed and water were culled to relieve suffering at the discretion of the Investigator. Bird weight, day of removal, reason for culling, and necropsy findings (including sex) of all dead and culled birds were recorded on pen mortality and necropsy records.

Birds were weighed on a pen basis on day 19 and at study end (day 53). Pens were selected and weighed in successive order by block.

Performance data has been summarized by average weight per bird on a pen basis. The average feed conversion was calculated for days 0–53 using the total feed consumption in a pen divided by the total weight gain of surviving birds.

Adjusted feed conversion was calculated using the total feed consumption in a pen divided by the total weight gain of surviving birds and weight of birds that died or were removed in that pen.

A recent field isolate of $E.$ $maxima$ was propagated, sporulated and suspended in distilled water prior to infecting the birds. At 13 days of age birds in each pen were orally administered the $Eimeria$ $oocysts$ via the feed.

At 19 days of age (6 days post challenge with $E.$ $maxima$) 4 birds were randomly (arbitrarily) selected from each pen for intestinal lesion scoring. At 28, 35, 41 and 53 days of age, 2 birds were randomly (arbitrarily) selected from each pen and scored for intestinal coccidiosis lesions.

The intestinal lesions were scored according to the method of Johnson and Reid in $Experimental$ $Parasitology,$ 28:30–36 91970. Lesions were scored for all four intestinal zones (upper, middle, lower and ceca) regardless of the fact that birds were infected only with $Eimeria$ $maxima$.

After the birds had been weighed on day 53, 8 male birds were selected for processing from each pen. The selected birds weighed within approximately ±5% of the average male bird weight for each particular treatment group. A total of 320 male birds (80/treatment) were processed. Processing was done on the first day following the day final weights were obtained. Processing data included the following: live weight (individual); hot weight (individual); chill weight (individual); and breast meat weight (individual).

In evaluating the test results, the following data was collected for broilers: body weights by pen on days 19 and 53; feed amounts added and removed from each pen days 0 through study end and calculated feed efficiency and adjusted feed efficiency; mortality: sex, weight, and probable cause of death; removed birds: reason for culling, sex, and weight; daily observations of facility and birds, daily facility temperature; intestinal lesion scores at 19, 28, 35, 41, 53 days of age; and processing yield at 54 days of age (80 birds/treatment).

The results are shown in Table XIII for each of the treatments.

TABLE XIII

| | Treatments | | | |
|---|---|---|---|---|
| | Control | 2 | 3 | Inv |
| Average Body weight (kg) | 2.548 | 2.548 | 2.592 | 2.595 |
| Adjusted Feed Efficiency (feed gain) | 1.990 | 1.983 | 1.991 | 1.956 |
| Mortality | 10.82% | 9.88% | 8.51% | 7.65% |
| Breast Meat Yield | 20.69% | 21.18% | 20.94% | 20.82% |
| Coccidiosis Lesion Score (average) | 2.00 | 1.92 | 1.86 | 1.66 |

From the above table, several observations are important. First, the test birds using the invention ended up weighing more than the controls and provided actually higher weights than other products of the assignee made from zinc salts and pure amino acids. Secondly, the adjusted feed efficiency was best of all products showing the largest weight gain per pound. Mortality was low, and the breast meat yield was comparable to the other products of the assignee. The coccidiosis lesion score was lowest, showing that the product truly was bioavailable to the chicken.

EXAMPLE 13

(Bioavailability of Zinc Using Chick Bioassay).

In these tests a conventional broiler feed mix was used. One batch was mixed, and the test diets were added to portions of the original mix. The test diets were as follows: (1) negative control; (2) zinc sulfate (5 to 40 ppm); (3) zinc methionine (5 to 20 ppm); and (4) invention or zinc amino acid complex (5 to 20 ppm).

The male broiler chicks one day of age were obtained from ConAgra Hatchery at Hurlock, Md. The objective of the study was to establish the zinc efficiency and the relative bioavailability values for each test diet. Table XIV shows the results.

TABLE XIV

| Zinc Source | Body Weight | Feed:Gain | Plasma Zinc | Bone Ash | Bone Zinc |
|---|---|---|---|---|---|
| Zinc Sulfate | 100.00 | 100.00 | 100.00 | 100.00 | 100.00 |
| Zinc Methionine | 141.86 | 139.61 | 124.43 | 121.24 | 133.18 |
| Inv:Zinc Amino Acid Complex | 149.30 | 140.44 | 127.57 | 128.90 | 137.42 |

The animals were all sacrificed after 21 days of feeding. The tibia was measured for bone ash and bone zinc. The zinc sulfate using none of the products of the assignee was used as the standard and arbitrarily assigned a rating of 100.

From the above test results, it can be seen that comparison with the zinc sulfate control the product of the invention performed superior in terms of bioavailability as measured by the bone zinc.

From the above examples it can be seen that applicant has prepared from protein starting materials pure metal amino acid complexes that are the full equivalent of those prepared from the pure amino acid compound and, of course, at substantially reduced cost. It therefore can be seen that the invention accomplishes at least all of its stated objectives.

What is claimed is:

1. A method of preparing in high yield a metal amino acid complex from protein starting material, comprising;

hydrolyzing a protein starting material to provide an amino acid hydrolysate, wherein the hydrolyzing conditions are at a temperature within the range of 140° C. to 160° C., a pressure within the range of 40 psi to 80 psi, and a hydrolyzing time of from about 1 hour to 3 hours; and thereafter adding a metal oxide to said amino acid hydrolysate to form a metal amino acid complex.

2. The process of claim 1 wherein the metal is selected from the group consisting of zinc, copper, manganese, iron, cobalt and chromium.

3. The method of claim 1 wherein the protein starting material is selected from the group consisting of feather meal, corn gluten meal, soybean meal, soy protein concentrate, blood meal, fish meal, casein, meat and bone meal, peanut meal, poultry byproduct meal, sunflower meal, dried yeast, and other protein meals of vegetable or animal origin.

4. The method of claim 3 wherein a metal oxide complex is a metal oxide of zinc, copper, manganese, iron, cobalt and/or chromium.

5. The method of claim 1 wherein the hydrolyzing of the protein starting material is by use of a strong inorganic acid.

6. The method of claim 1 wherein the strong inorganic acid is selected from the group consisting of hydrochloric, sulfuric and phosphoric acid.

7. The method of claim 6 wherein the strong inorganic acid is used at a 6 normal acid, approximately 2 equivalents.

8. The method of claim 1 wherein the hydrolyzing time is up to about 1 hour.

9. The method of claim 1 wherein an additional step comprises raising the pH from an acid pH to a pH within the range of about 4 to 5 with an alkali or an alkaline earth hydroxide.

10. The method of claim 1 wherein the yield of protein is at a conversion of the protein starting material to pure protein, the profile consistent with the protein profile starting material, but at a pure acid yield conversion of 90% or higher.

11. The method of claim 1 which includes as an additional step, adding the metal amino acid complex derived from the protein starting material to an absorbent carrier to provide the final supplementation product.

12. The method of preparing in high yield a metal amino acid complex from protein starting material, comprising:

hydrolyzing a protein starting material to provide an amino acid hydrolysate; and thereafter adding a metal oxide to said amino acid hydrolysate to form a metal amino acid complex, said metal oxide corresponding to the metal moiety desired for the metal amino acid complex; and thereafter adjusting the pH of said metal amino acid complex to a pH within the range of about 4 to about 5; and finally, adding an absorbent carrier to said metal amino acid complex to provide the final supplement that will supplement trace mineral metals and amino acids in highly bioavailable form for livestock.

13. A method of preparing in high yield a metal amino acid complex from protein starting material, comprising:

hydrolyzing a protein starting material to provide an amino acid hydrolysate, wherein the hydrolyzing conditions include utilizing a high pressure of approximately 40 psi to 80 psi; and thereafter adding a metal oxide to said amino acid hydrolysate to form a metal amino acid complex.

14. The method of claim 13 wherein the pressure is about 50 psi.

* * * * *